(12) United States Patent
Marzano et al.

(10) Patent No.: US 9,692,173 B2
(45) Date of Patent: Jun. 27, 2017

(54) FEEDTHROUGH WIRE CONNECTOR FOR USE IN A MEDICAL DEVICE

(71) Applicant: Greatbatch Ltd., Clarence, NY (US)

(72) Inventors: Thomas Marzano, East Amherst, NY (US); Keith W. Seitz, Clarence Center, NY (US); Michael F. Scalise, Clarence, NY (US)

(73) Assignee: Greatbatch Ltd., Clarence, NY (US)

( * ) Notice: Subject to any disclaimer, the term of this patent is extended or adjusted under 35 U.S.C. 154(b) by 189 days.

(21) Appl. No.: 14/747,582

(22) Filed: Jun. 23, 2015

(65) Prior Publication Data

US 2015/0295349 A1    Oct. 15, 2015

Related U.S. Application Data

(63) Continuation-in-part of application No. 13/487,293, filed on Jun. 4, 2012, now Pat. No. 9,065,224.
(Continued)

(51) Int. Cl.
*H01R 13/52* (2006.01)
*H01G 4/35* (2006.01)
(Continued)

(52) U.S. Cl.
CPC ....... *H01R 13/5224* (2013.01); *A61N 1/3754* (2013.01); *H01G 4/35* (2013.01);
(Continued)

(58) Field of Classification Search
CPC .......................... H01R 13/426; H01R 13/5224
(Continued)

(56) References Cited

U.S. PATENT DOCUMENTS 2,685,073 A   7/1954  Damon
3,200,355 A   8/1965  Dahlen
(Continued)

OTHER PUBLICATIONS

EPSearch, "12170625.3", Oct. 4, 2012, Oct. 4, 2012.

*Primary Examiner* — James Harvey
(74) *Attorney, Agent, or Firm* — Steven W. Winn; Michael F. Scalise

(57) ABSTRACT

A feedthrough filter capacitor assembly comprising a terminal pin connector is described. The terminal pin connector is designed to facilitate an electrical connection between the terminal pin comprising a multitude of compositions to a circuit board of an implantable medical device. The terminal pin connector comprises a clip portion positioned within a connector housing. The connector clip mechanically attaches to the terminal pin of the feedthrough with at least one prong and an exterior surface of the connector housing electrically contacts the circuit board, creating an electrical connection therebetween. The connector housing comprises a material that is conducive to a weld or solder attachment process to the circuit board. The feedthrough filter capacitor assembly is particularly useful for incorporation into implantable medical devices such as cardiac pacemakers, cardioverter defibrillators, and the like, to decouple and shield internal electronic components of the medical device from undesirable electromagnetic interference (EMI) signals.

37 Claims, 9 Drawing Sheets

Related U.S. Application Data

(60) Provisional application No. 61/492,828, filed on Jun. 3, 2011.

(51) Int. Cl.
    *A61N 1/375*     (2006.01)
    *H01R 13/426*     (2006.01)
    *H01R 13/719*     (2011.01)

(52) U.S. Cl.
    CPC ......... *H01R 13/426* (2013.01); *H01R 13/521* (2013.01); *H01R 13/719* (2013.01); *Y10T 29/49204* (2015.01)

(58) Field of Classification Search
    USPC ................ 439/252, 379, 675, 834, 904, 931
    See application file for complete search history.

(56) References Cited

U.S. PATENT DOCUMENTS

| | | |
|---|---|---|
| 4,187,605 A * | 2/1980 | Selvin ............... H01R 13/426 29/838 |
| 4,421,378 A | 12/1983 | Sanford et al. |
| 4,767,342 A | 8/1988 | Sato |
| 5,055,055 A | 10/1991 | Bakker |
| 5,103,818 A | 4/1992 | Maston et al. |
| 5,376,012 A | 12/1994 | Clark |
| 5,591,039 A | 1/1997 | Matthews |
| 6,852,925 B2 * | 2/2005 | Wolf ....................... H01M 2/06 174/50.56 |
| 6,932,658 B2 | 8/2005 | Liang |
| 7,038,900 B2 † | 5/2006 | Stevenson |
| 7,172,467 B1 | 2/2007 | Yohn et al. |
| 7,630,768 B1 | 12/2009 | Coffed et al. |
| 7,794,256 B1 | 9/2010 | Sochor |
| 7,812,691 B1 | 10/2010 | Fisk et al. |
| 7,931,507 B2 | 4/2011 | Yu et al. |
| 8,112,152 B2 † | 2/2012 | Taylor |
| 8,642,887 B1 | 2/2014 | Li et al. |
| 2003/0139096 A1 | 7/2003 | Stevenson et al. |
| 2006/0167522 A1 | 7/2006 | Malinowski |
| 2006/0221543 A1 | 10/2006 | Stevenson et al. |
| 2007/0134985 A1 | 6/2007 | Frysz et al. |
| 2007/0203530 A1 | 8/2007 | Hubing et al. |
| 2007/0260282 A1 | 11/2007 | Taylor et al. |
| 2009/0259265 A1 | 10/2009 | Stevenson et al. |
| 2010/0192355 A1 | 8/2010 | Zhao et al. |
| 2011/0106189 A1 | 5/2011 | Seeley et al. |
| 2011/0303458 A1 | 12/2011 | Sutay et al. |
| 2012/0309237 A1 | 12/2012 | Marzano et al. |
| 2015/0295349 A1 * | 10/2015 | Marzano .............. H01R 13/426 439/283 |

\* cited by examiner
† cited by third party

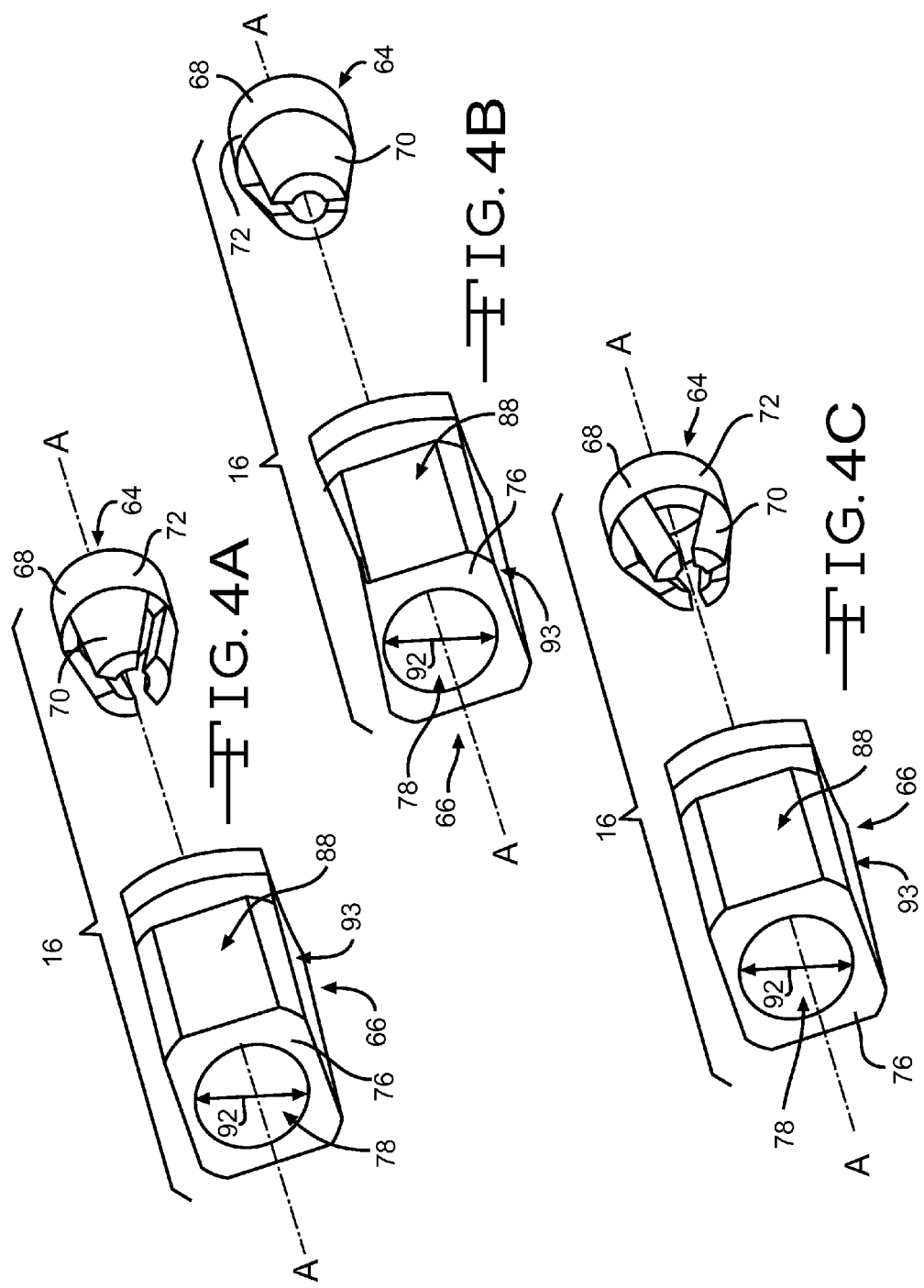

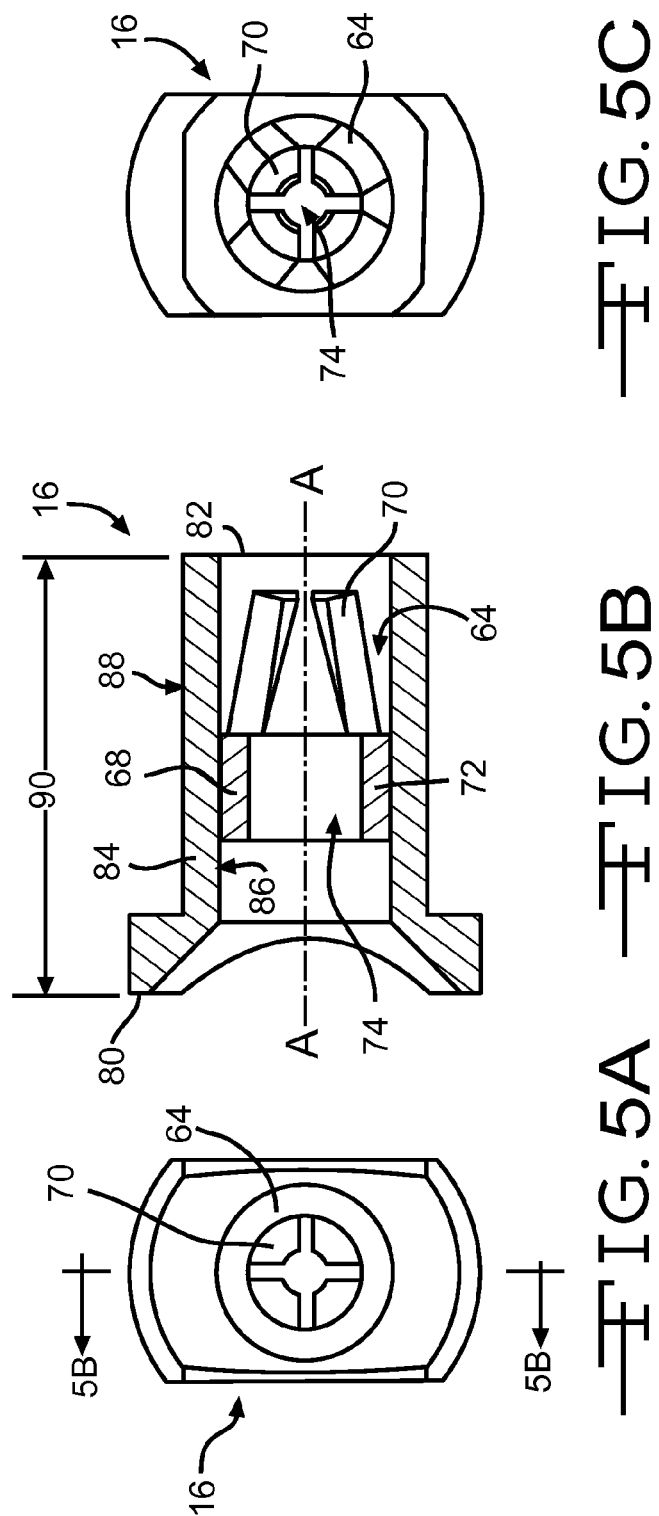

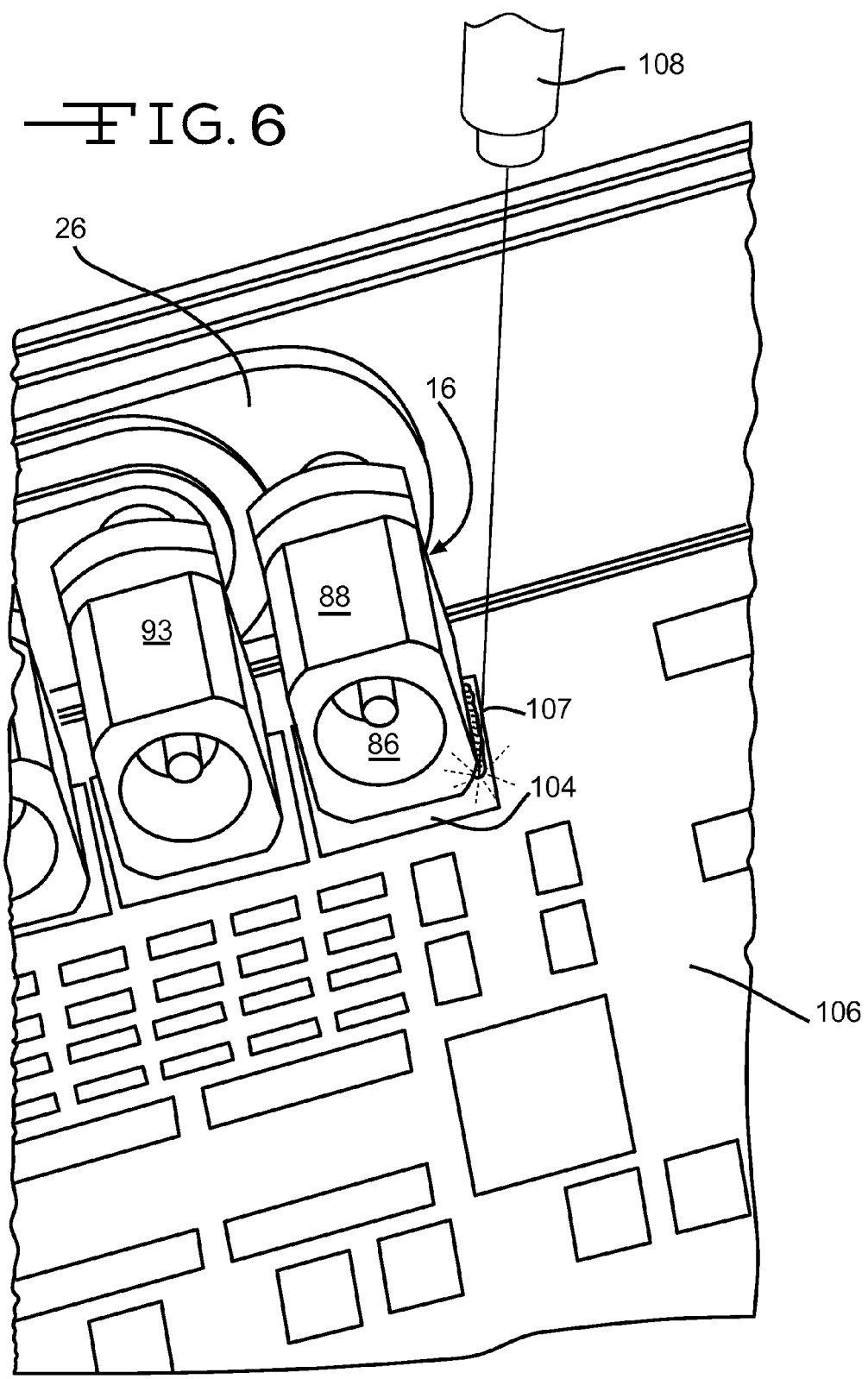

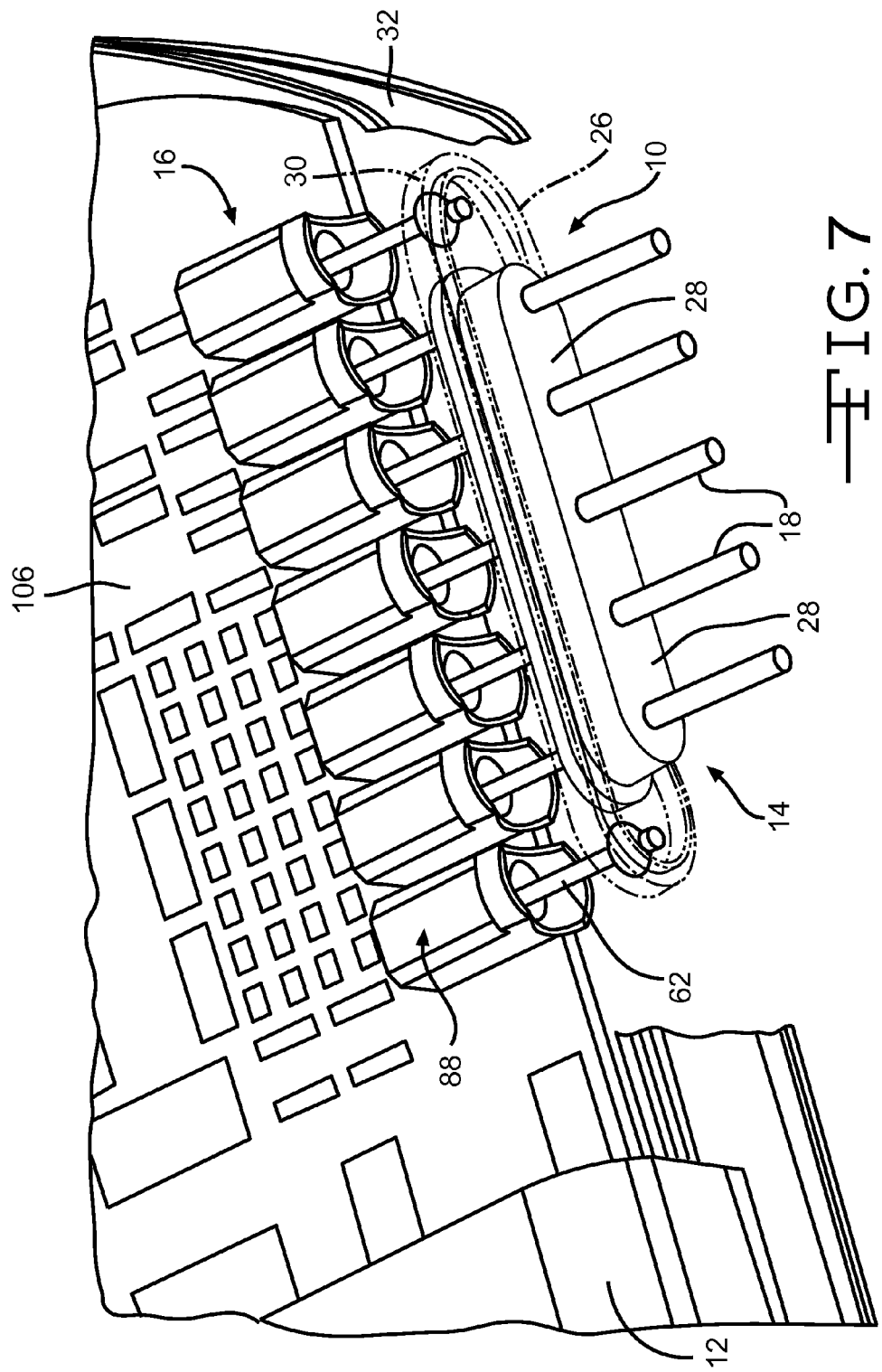

FEEDTHROUGH WIRE CONNECTOR FOR USE IN A MEDICAL DEVICE

CROSS REFERENCE TO RELATED APPLICATIONS

This application is a continuation in part of U.S. utility application Ser. No. 13/487,293, filed on Jun. 4, 2012, now U.S. Pat. No. 9,065,224, which claims priority to U.S. provisional application Ser. No. 61/492,828, filed on Jun. 3, 2011.

FIELD OF THE INVENTION

This invention relates generally to a hermetic feedthrough terminal pin assembly, preferably of the type incorporating a filter capacitor. More specifically, this invention relates to a connector assembly comprising a clip positioned within a housing for incorporation into feedthrough filter capacitor assemblies, particularly of the type used in implantable medical devices such as cardiac pacemakers, cardioverter defibrillators, and the like. That is to facilitate connection of the feedthrough terminal pin to a circuit board within the implantable medical device.

BACKGROUND OF THE INVENTION

Feedthrough assemblies are generally well known in the art for use in connecting electrical signals through the housing or case of an electronic instrument. For example, in an implantable medical device, such as a cardiac pacemaker, defibrillator, or neurostimulator, the feedthrough assembly comprises one or more conductive terminal pins supported by an insulator structure for passage of electrical signals from the exterior to the interior of the medical device. The conductive terminals are fixed into place using a metallization and gold braze process, which provides a hermetic seal between the pin and insulative material.

Conventionally, a distal end portion of the terminal pin is electrically connected directly within the implantable medical device. In this case, the distal end portion of the terminal pin is electrically connected directly to an electrical circuit residing within the device by using a soldering or welding attachment process. This connection is readily achievable utilizing platinum or platinum alloy based terminal pins of the prior art. However, the cost of these platinum based terminal pins is prohibitively costly to manufacture. As a result, other lower cost metals such as niobium, tantalum and titanium are increasingly being utilized in replacement of platinum and platinum alloy based terminal pins. These alternative materials provide adequate electrical conduction, however, their specific material properties make them difficult to weld or solder to the electrical contacts of a circuit board. The electrical contacts of the circuit board are typically comprised of gold or copper which are known to be readily solderable and weldable metals.

The present invention, therefore, facilitates the electrical connection of the terminal pin to the circuit board by providing a connector that enables an improved connection of the feedthrough terminal pin, regardless of its composition. The terminal pin connector of the present invention comprises a clip that is encompassed within a housing. The clip is positioned circumferentially around the terminal pin and is designed to grip the terminal pin in such a way as to prevent the pin from moving proximally or distally out of the connector.

The connector housing comprises an annular sidewall with an outer surface designed to establish physical contact with the circuit board, providing electrical connection therebetween. The outer surface of the connector housing sidewall may be constructed of, or coated with, an electrically conductive material that is conducive to soldering and/or welding attachment processes. Therefore, the present invention provides a feedthrough with an improved electrical connection between its terminal pin or pins and the circuit board of an implantable medical device, for a multitude of terminal pin compositions.

SUMMARY OF THE INVENTION

In a preferred form, a feedthrough filter capacitor assembly according to the present invention comprises an outer ferrule hermetically sealed to either an alumina insulator or fused glass dielectric material seated within the ferrule. The insulative material is also hermetically sealed to at least one terminal pin. That way, the feedthrough assembly prevents leakage of fluid, such as body fluid in a human implant application, past the hermetic seal at the insulator/ferrule and insulator/terminal pin interfaces.

According to the invention, a connector is affixed to a distal end portion of at least one of the terminal pins of the feedthrough. The connector comprises a clip that resides within a connector housing. The clip is design to grasp the outer perimeter of the terminal pin, thus preventing the clip from moving in relation to the pin. The connector housing comprises a annular sidewall that surrounds and encompasses the clip therewithin.

In a preferred embodiment, the sidewall of the connector housing comprises an electrically conductive interior and external surface that establishes an electrical connection between a circuit board of an implantable medical device and the terminal pin of the feedthrough. The sidewall of the connector housing can either be constructed of an electrically conductive material, or alternatively, a portion of the exterior and interior surfaces of the connector sidewall, such as by a coating composed of an electrically conductive material. It is preferred that the material with which the connector sidewall is constructed or coated, is conducive to solder or welding attachment processes. Once the connector pin and feedthrough assembly are positioned within the implantable medical device, a portion of the exterior surface of the sidewall of the connector is positioned such that it establishes electrical contact within the implantable medical device. More preferably, a portion of the exterior surface of the sidewall of the connector housing is soldered or welded to a circuit board positioned within a medical device. This joined connection, therefore, establishes an electrical connection between the circuit board and the terminal pin of the feedthrough, through the connector housing sidewall.

These and other objects and advantages of the present invention will become increasingly more apparent by a reading of the following description in conjunction with the appended drawings.

BRIEF DESCRIPTION OF THE DRAWINGS

FIGS. 4A-4C illustrate different embodiments of the clip portion of the connector feature.

FIG. 5A shows a proximal end view of an embodiment of the connector feature.

FIG. 5B is a cross-sectional view of the connector feature shown in FIG. 5A.

FIG. 5C shows a distal end view of the connector feature shown in FIG. 5A.

FIG. 6 illustrates an embodiment of the connector feature being joined to a conductor pad of a circuit board.

FIG. 7 shows a magnified partial cross-sectional view of an embodiment of the feedthrough connector assembly positioned within an implantable medical device.

DETAILED DESCRIPTION OF THE PREFERRED EMBODIMENTS

Figure 1:
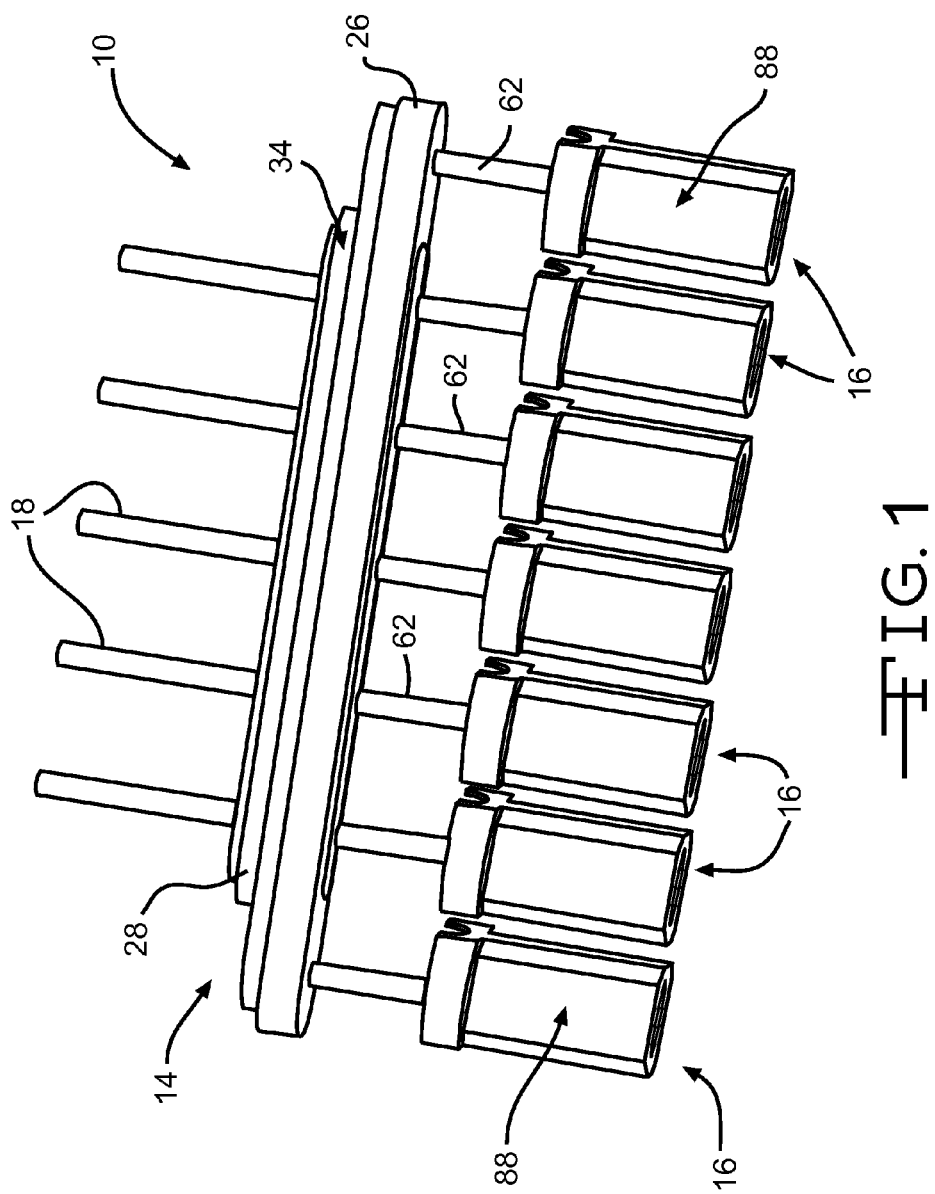
FIG. 1 illustrates a side view of an embodiment of the feedthrough connector assembly of the present invention.

Referring now to the drawings, FIGS. 1, 2, 3, 7, and 7A illustrate an embodiment of a feedthrough connector assembly 10 of the present invention. The feedthrough connector assembly 10 is useful with medical devices, preferably an active implantable medical device (AIMD) 12 (FIG, 7A) such as a pacemaker, cardiac defibrillator, cardioverter defibrillator, cochlear implant, neurostimulator, internal drug pump, deep brain stimulator, hearing assist device, incontinence device, obesity treatment device, Parkinson's disease therapy device, bone growth stimulator, and the like. As shown, the connector assembly 10 comprises a feedthrough 14 portion and a terminal pin connector portion 16.

The feedthrough 14 portion of the assembly 10 includes terminal pins 18 that provide for coupling, transmitting and receiving electrical signals to and from body tissue, such as a patient's heart, while hermetically sealing the interior of the medical instrument against ingress of patient body fluids that could otherwise disrupt instrument operation or cause instrument malfunction.

Figure 3:
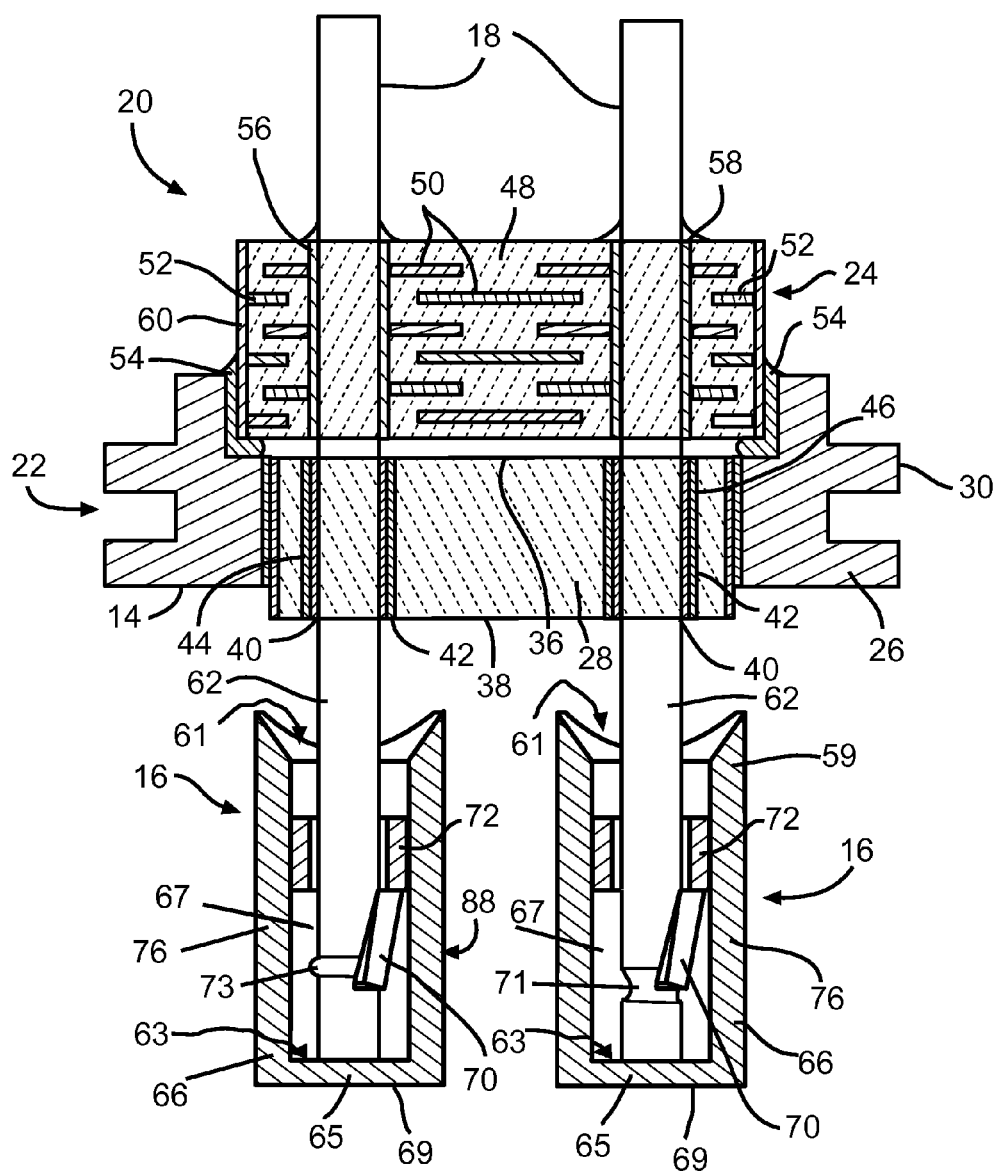
FIG. 3 shows a cross-sectional view of an embodiment of the feedthrough connector assembly of the present invention.

FIG. 3 illustrates a cross-sectional view of a preferred embodiment of an internally grounded feedthrough capacitor connector assembly 20 of the present invention. As illustrated the internally grounded feedthrough capacitor connector assembly 20 comprises a filter feedthrough capacitor assembly 22 comprising a capacitor 24 that is attached to the feedthrough portion 14. Like the feedthrough connector assembly 10, the feedthrough capacitor connector assembly 20 comprises a connector portion 16. While not necessary for accomplishing these functions, the filter capacitor 24 is attached to the feedthrough 14 for suppressing or decoupling undesirable electro-magnetic interference (EMI) signals and noise transmission into the interior of the medical device.

Figure 7A:
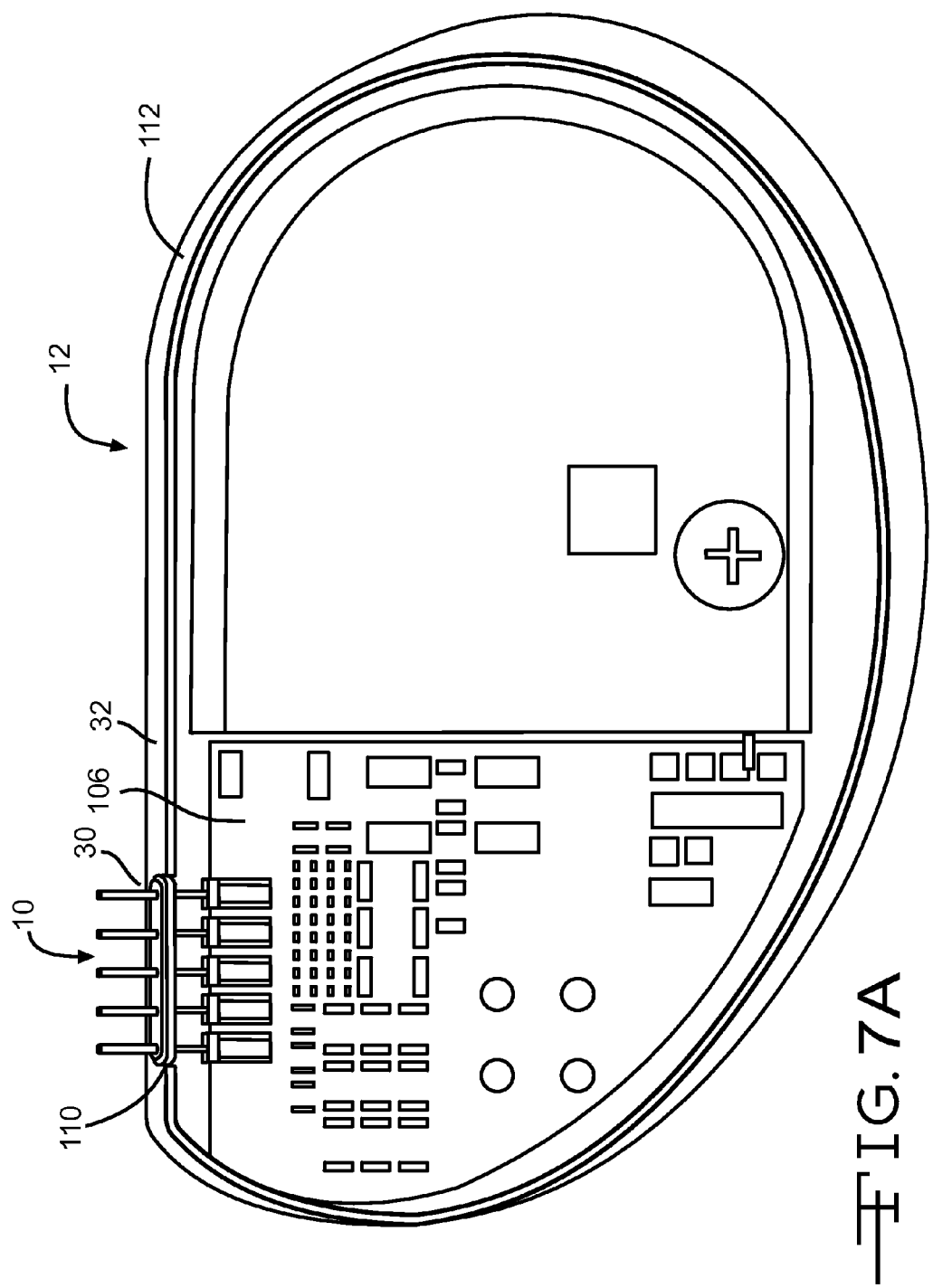
FIG. 7A illustrates a cross-sectional view of an embodiment of a feedthrough connector assembly of the present invention positioned within an implantable medical device.

More particularly, the feedthrough 14 of the feedthrough connector assembly 10 and the feedthrough filter capacitor assembly 22, comprises a ferrule 26 defining an insulator-receiving bore surrounding an insulator 28. Suitable electrically conductive materials for the ferrule 26 include titanium, tantalum, niobium, stainless steel or combinations of alloys thereof, the former being preferred. The ferrule 26 may be of any geometry, non-limiting examples being curved, round, rectangle, and oblong. A surrounding flange 30 extends from the ferrule 26 to facilitate attachment of the feedthrough 14 to a casing 32 of the implantable medical device 12 as previously described (FIGS. 7 and 7A). The method of attachment may be by laser welding, soldering or other suitable methods.

The insulator 28 is of a ceramic material such as of alumina, zirconia, zirconia toughened alumina, aluminum nitride, boron nitride, silicon carbide, glass or combinations thereof. Preferably, the insulating material is alumina, which is highly purified aluminum oxide, and comprises a sidewall 34 extending to a first upper side 36 and a second lower side 38. The insulator 28 is also provided with bores 40 that receive the terminal pins 18 passing therethrough. A layer of metal 42, referred to as metallization, is applied to the insulator sidewall 34 and a bore sidewall 44 of the terminal pin bores 40 to aid a braze material 46 in hermetically sealing between the ferrule 26 and the sidewall 34 of the insulator 28 and between the terminal pins 18 and the bore sidewall 44 of the insulator 28, respectively. Specifically, the metallization layer 42 is preferably applied to a portion of the outer surface of the insulator sidewall 34 and a portion of the surface of the inside sidewall 44 of the terminal pin bores 40. These surfaces are intended to contact and bond with the ferrule 26 and terminal pins 18 respectively of the feedthrough assembly 14, establishing a hermetic seal therebetween.

As further shown in FIG. 3, the feedthrough filter capacitor assembly 22 includes the filter capacitor 24 that provides for filtering undesirable EMI signals before they can enter the device housing via the terminal pins 18. The filter capacitor 24 comprises a ceramic or ceramic-based dielectric monolith 48 having multiple capacitor-forming conductive electrode plates formed therein. The capacitor dielectric 48 preferably has a circular cross-section matching the cross-section of the ferrule 26 and supports a plurality of spaced-apart layers of first or "active" electrode plates 50 in spaced relationship with a plurality of spaced apart layers of second or "ground" electrode plates 52. Alternatively, the capacitor dielectric 48 may have an oval or rectangular cross-section that approaches the cross-section shape of the ferrule 26. The filter capacitor 24 is preferably joined to the feedthrough 14 adjacent to the insulator upper side 36 by a bead 54 of conductive material, such as a solder or braze ring, or a thermal-setting conductive adhesive, and the like. The dielectric 48 includes lead bores 56 provided with an inner surface metallization layer. The terminal pins 18 pass therethrough and are conductively coupled to the active plates 50 by a conductive braze material 58 contacting between the terminal pins 18 and the bore metallization. In a similar manner, the ground plates 52 are electrically connected through an outer surface metallization 60 and the conductive material 54 to the ferrule 26.

As shown in FIGS. 1, 3, 6, 7 and 7A, the terminal pin connector 16 of the present invention is attached to at least one terminal pin 18 of the feedthrough 14. The terminal pin connector 16 may be attached to the terminal pin 18 of either an unfiltered feedthrough assembly 14, as shown in FIGS. 1-2, 6, 7 and 7A, or the feedthrough filter capacitor assembly 22, as illustrated in FIG. 3. More specifically, the connector portion 16 is attached to a distal end portion 62 of the terminal pin 18. For identification purposes, the distal end portion 62 of the terminal pin 18 is defined as the portion of the terminal pin 18 that resides within the active implantable medical device (AIMD) 12.

As illustrated in FIGS. 3, 4, 4A-4C and 5A-5C, the terminal pin connector 16 comprises a clip 64 that resides within a connector housing 66. The clip 64 is designed to be positioned around the perimeter of the terminal pin 18 such that the clip 64 grasps the exterior surface of the terminal pin 18. In one embodiment shown in FIGS. 4A-4C, and 5B, the clip 64 comprises a clip base portion 68 with at least one prong 70 extending from the base 68. As shown, the clip base portion 68 comprises an annular sidewall 72 which encompasses a clip base portion throughbore 74. This throughbore 74 is the opening through which the terminal pin 18 longitudinally extends. The base throughbore 74 is dimensioned such that the terminal pin 18 of a multitude of diameters can pass therethrough.

As shown in FIGS. 3 and 4A-4C, the clip 64 comprises at least one prong or finger 70 that extends from the base portion 68. As shown, the prong or prongs 70 are preferably angled inwardly towards a longitudinal axis A-A (FIG. 5B) that extends longitudinally through the throughbore 74 of the base portion 68. This inward orientation enables the prong or prongs 70 to contact and compress against the exterior surface of the perimeter of the terminal pin 18 gripping the pin 18 therewithin. In addition, the inward orientation of the prong 70 creates a wedging relationship between the terminal pin 18 and the base clip annular sidewall 72. As the end of the prong 70 compresses against the sidewall of the terminal pin 18, the pin 18 becomes wedged between the prong 70 and the bottom edge of the sidewall 72. Such a wedging relationship helps prevent the terminal pin 18 from disengaging with the clip 64.

As the terminal pin 18 is introduced through the base portion 68 of the clip 64, the space between the prong(s) 70 expands to thereby allow the terminal pin 18 to proceed therebetween. The prong(s) 70 of the clip 64 are preferably designed to allow the terminal pin 18 to proceed in one direction between the prong end(s) such that the terminal pin 18 is prohibited from moving in the reverse direction. In a preferred embodiment, the terminal pin 18 proceeds in a distal direction through the throughbore 74 of the clip 64 residing within the connector housing 66. Once positioned within the throughbore 74, the angled prong orientation grips the pin 18 and prevents it from moving in the reverse proximal direction.

FIG. 3 illustrates an alternative embodiment of a clip 64 and connector housing 66 assembly of the present invention. As shown, a single prong 70 extends from the base portion 68 of the clip 64. In addition, the connector housing 66 comprises an opening 67 that partially extends through the thickness of the housing 66 from a first housing end 59 towards a second housing end 69. The opening 67 has a first diameter that extends through the first housing end 59. The opening 67 extends axially along longitudinal axis A-A through a portion of the housing thickness to an end wall 65 located at the second housing end 69, thereby forming a blind hole 67 within the connector housing 66. As defined herein a "blind hole" is a hole that is formed such as by reaming, drilling, or milling to a specified depth without breaking through the end wall 65 of the work piece.

In a preferred embodiment, at least a portion of the distal end 62 of the terminal pin 18 is positioned within the blind hole 67 that extends along longitudinal axis A-A. In a preferred embodiment, the distal end 62 of the terminal pin 18 is positioned within the blind hole 67 proximate an interior surface 63 of the end wall 65.

In addition, a single prong 70 is shown extending distally from the annular sidewall 72. In a preferred embodiment, the end of the prong 70 contacts a portion of an exterior surface of the terminal pin 18 along the distal end portion 62 that resides within the opening 67. This is to help prevent inadvertent movement of the terminal pin 18 along the longitudinal axis A-A out from within the connector opening 67. The prong 70 is preferably angled inwardly towards the central axis A-A that extends longitudinally through the throughbore 74 of the base portion 68 and into the blind hole 67. As previously mentioned, this inward orientation enables the prong 70 to contact and compress against the exterior surface of the perimeter of the terminal pin 18 gripping the pin 18 therewithin. Furthermore, the prong 70 creates a wedging relationship between the exterior surface of the terminal pin 18 and the annular sidewall 72.

In a preferred embodiment, a recess 71, such as the recess illustrated in FIG. 3, may partially extend within an external terminal pin surface about the distal pin portion 62 thereof. More preferably, the recess 71 is positioned such that it annularly extends around the circumference of the pin 18 within the distal pin portion 62. The recess 71 preferably enhances the grip of the prong 70 along the pin's exterior surface by providing a groove within the exterior pin surface for the end of the prong 70 to be positioned therewithin. Thus, the recess 71 helps prevent the pin 18 from becoming disengaged from the clip 64. In addition, the recess 71 helps prevent the connector housing 66 from undesirably moving in a distal axial direction such that it might slide off the distal end of the terminal pin 18.

Alternatively, in lieu of the recess 71, an outwardly extending ridge 73 may be constructed about the distal portion 62 of the terminal pin 18. Like the recess 71, the ridge 73 may be positioned such that it annularly extends around the circumference of the pin 18 within the distal end portion 62. Like the recess 71, the outwardly extending ridge 73 helps prevent disengagement of the clip 64 from the terminal pin 18. In a preferred embodiment, when the pin 18 is positioned within the connector housing 66, the ridge 73 is preferably positioned proximal of the end of the prong 70. This way, the ridge 73 enhances the grip of the prong 70 on the exterior surface of the pin 18 and helps prevent unintentional distal axial movement of the connector housing 66 that would disengage it from the terminal pin 18.

The connector clip 64 is preferably composed of an electrically conductive material, such as an electrically conductive metal. The connector clip 64 is designed to provide an electrical connection between the terminal pin 18 of the feedthrough 14 and the connector housing 66. In a preferred embodiment, the clip 64 may be constructed from copper, tin, stainless steel, aluminum, titanium, gold, platinum, palladium, palladium alloys, associated alloys and combinations thereof.

As shown in FIGS. 1, 4, 4A-4C, 5A-5C, 7 and 7A, the connector housing 66 comprises an annular sidewall 76 which encompasses a housing throughbore 78 or blind opening 67 (FIG. 3) that extends longitudinally therethrough. In the embodiment shown, the housing 66 is designed similarly to that of a tube having an opening that extends from a proximal housing end 80 to a distal housing end 82. The connector housing 66 comprises a sidewall thickness 84 that extends from an interior sidewall surface 86 to an exterior sidewall surface 88. In a preferred embodiment, the terminal pin connector 16 has a length 90 ranging from about 0.25 inches to about 2.0 inches and a throughbore diameter 92 that ranges from about 0.1 inches to about 0.25 inches.

Figure 2:
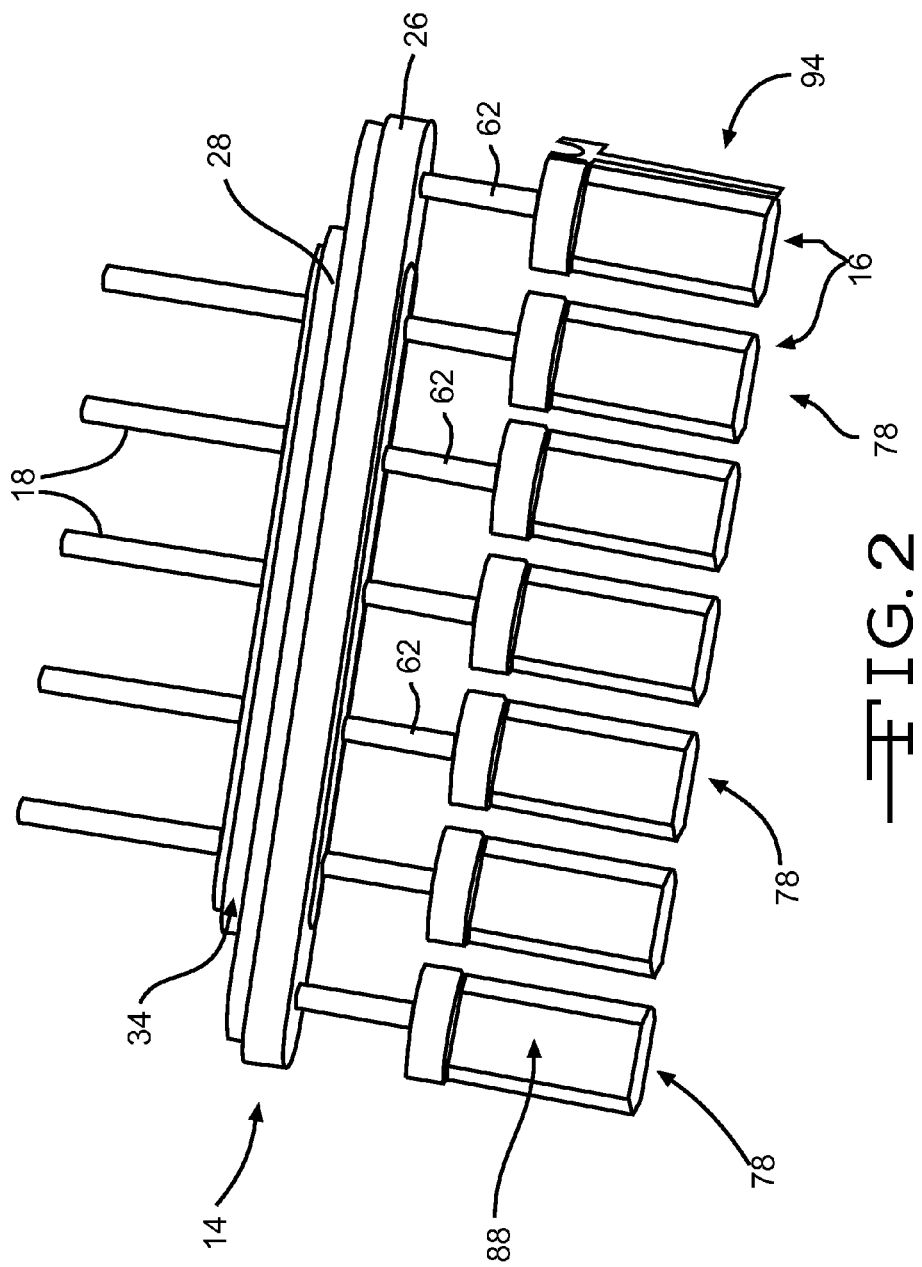
FIG. 2 illustrates an alternate embodiment of the connector feedthrough connector assembly comprising a one-piece housing.

An individual clip 64 is preferably positioned within the throughbore 78 or blind hole 67 (FIG. 3) of each connector housing 66. This orientation prevents the clip 64 from moving within or out of the housing 66. Furthermore, this embodiment allows each of the terminal pins 18 to be bent in individual orientations. Alternatively, as shown in the embodiment of FIG. 2, the connector housing may be constructed of a one-piece housing body 94. In this embodiment, the connector housing body 94 comprises a one-piece construction having a plurality clips 64 positioned within each of the individual housing thoughbores 78. The housing throughbores 78 may be arranged in a linear orientation or they may be arranged in the form of a circle, oval, triangle, star or the like to match the cross-sectional form of the feedthrough 14.

Figure 4:
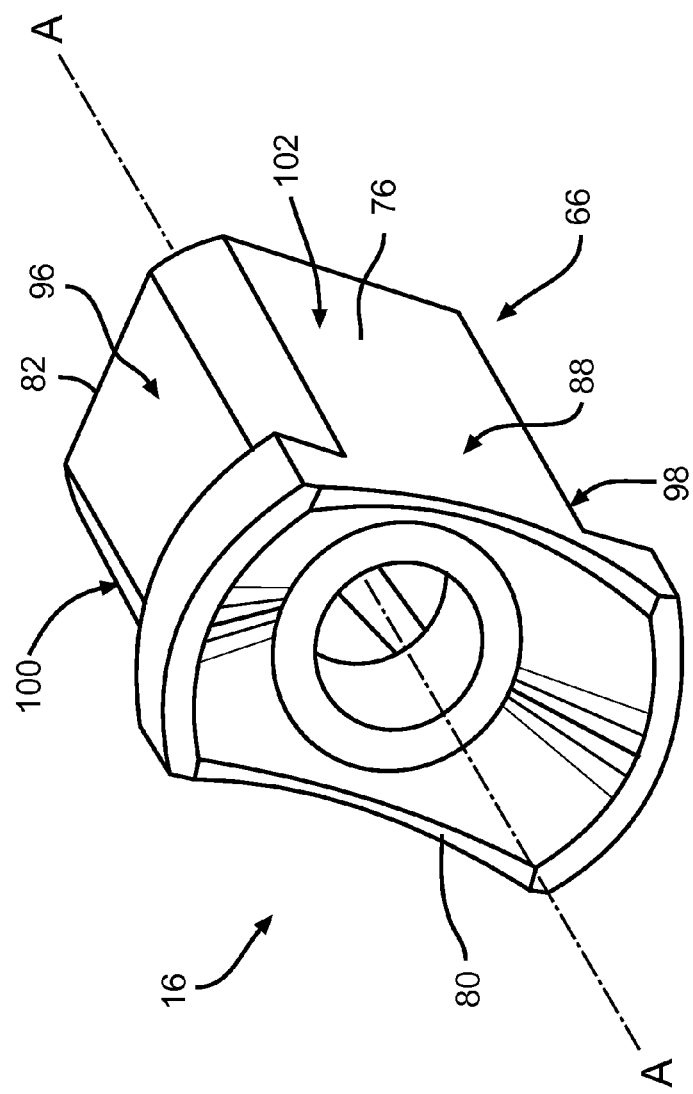
FIG. 4 shows a perspective view of an embodiment of the connector feature.

The exterior surface of the sidewall 88 of the connector housing 66 or one-piece housing body embodiment 94, is preferably constructed with at least one planar surface portion 93. As shown in FIG. 4, the illustrated embodiment of the connector housing 66 comprises four planar surface portions, a top planar surface 96, a bottom planar surface 98, a left side planar surface 100 and a right side planar surface 102 that extend at least part way along the longitudinal length of the housing 66. Alternatively, the connector housing 66 may comprise fewer or more exterior surface planar portions.

As illustrated in FIG. 6, the planar surface portion 93 of the exterior surface 88 of the housing 66 is designed to establish intimate electrical contact with an electrical contact pad 104 of a circuit board 106 of the medical device 12. As such, the connector housing 66 may be composed of an electrically conductive material or alternatively, is coated with an electrically conductive material, such as a metal.

In an embodiment, the exterior surface 88 of the connector housing 66 comprises a coating of an electrically conductive material. In a preferred embodiment, the coating is conducive for use in the joining processes of soldering or welding. The coating may comprise, but not be limited to, copper, tin, stainless steel, aluminum, titanium, gold, platinum, palladium, palladium alloys, associated alloys and combinations thereof.

Alternatively, a portion of the exterior surface 88 and a portion of the interior surface 86 of the sidewall 76 of the connector housing 66 may be constructed of an electrically conductive material, particularly a material that is conducive to the joining processes of soldering and/or welding. In either case, the connector housing 66 preferably enables an electrically conductive pathway that extends through at least a portion of the thickness 84 of the housing sidewall from the inner surface 86 of the housing 66 to the outer surface 88. The connector housing 66 is designed such that an electrical connection is made between the terminal pin. 18 of the feedthrough 14 portion and the circuit board 106 of the AIMD 12.

Once the connector feedthrough assembly 10 or filtered feedthrough connector assembly 20 is positioned within the AIMD 12, the exterior surface 88 of the connector housing 66 may be electrically joined to an electrically conductive pad or area 104 of the circuit board of the AIMD 12 by a weld 107. As shown in FIG. 6, a joining instrument 108, such as a laser welding or soldering instrument, may be utilized to join a portion of the exterior housing surface 88 to the circuit board pad 104. Although it is preferred that the exterior surface of the housing 66 of the connector 16 is permanently joined to the electrical contact pad 104 of the circuit board 106, the exterior surface 88 of the housing 66 of the connector may be placed in contact with the surface of the electrical contact pad 104, without the joining weld 107, such that it may be easily removed. For example, once the terminal pin connector(s) are positioned over the terminal pin(s), the terminal pin(s) may be bent such that the exterior surface 88 of the housing 66 is in a removeable contactable relationship with the surface of the electrical contact pad 104 of the circuit board 106.

The feedthrough connector assembly 10 or filtered feedthrough connector assembly 20 is preferably designed to be utilized with a "clam shell" style medical device casing 32. A "clam shell" type medical device casing 32 is one in which two opposing case halves come together to form the full casing In one embodiment, as illustrated in FIG. 7A, the feedthrough connector assembly 10 or filtered feedthrough connector assembly 20 is positioned within an inlet 110 of a first half 112 of the casing 32. The flange 30 is typically welded to casing half within the inlet 110 and the terminal pin connector(s) 16, attached to their respective terminal pins 18, are positioned on the circuit board pad(s) 104 of the circuit board 106. In a second embodiment, the terminal pin connector(s) 16 may be first positioned and joined either by welding or soldering 107 on the circuit board pad(s) 104 of the circuit board 106. After the terminal pin connector(s) 16 are positioned on their respective circuit board pad(s) 104, the terminal pins 18, are positioned within the terminal pin connector(s) 16. Once the terminal pins 18 are correctly positioned, the flange 30 of the feedthrough 14 is preferably welded to the first case half 112. In either embodiment, a second case half or case lid 114 (FIG. 7) is positioned adjacent to the first case half 112 such that their respective inlets 110 and sidewalls oppose each over. The respective first and second halves of the casing 32 are typically welded together establishing a hermetic seal therewithin.

It is appreciated that various modifications to the invention concepts described herein may be apparent to those of ordinary skill in the art without departing from the scope of the present invention as defined by the appended claims.

What is claimed is:

1. A feedthrough connector assembly, which comprises:
   a) an electrically conductive connector, comprising:
      i) a connector housing comprising a housing sidewall defining an opening surrounded by an inner surface of the housing sidewall, wherein the inner housing surface has a first length extending along a longitudinal axis to opposed first and second housing ends and wherein the inner housing surface has a first diameter for at least part of the first length; and
      ii) at least one prong supported by the housing sidewall, wherein the prong extends axially and inwardly along the longitudinal axis to a prong end that is closer to the axis than the first diameter of the inner housing surface;
   b) a hermetic feedthrough, comprising:
      i) an electrically conductive ferrule comprising a ferrule sidewall having an inner ferrule surface defining a ferrule opening, wherein the ferrule sidewall extends from a first ferrule end surface spaced from a second ferrule end surface;
      ii) an insulator disposed at least partially within and hermetically sealed to the inner ferrule surface, wherein the insulator comprises first and second insulator ends disposed adjacent to the respective first and second ferrule end surfaces;
      iii) at least one first bore extending through the insulator to the first and second insulator ends;
      iv) an electrically conductive terminal pin received in the first bore, the terminal pin having a terminal pin sidewall extending from a first terminal pin portion having a first terminal pin end to a second terminal pin end, wherein the opposed first and second terminal pin ends are spaced outwardly from the respective first and second insulator ends; and v) a first hermetic seal at the terminal pin to the insulator and a second hermetic seal at the insulator to the ferrule; and d) wherein the hermetic feedthrough is electrically connected to the connector with the first terminal pin portion residing within the housing so that the prong end contacts the terminal pin sidewall in a grip-tight engagement to thereby help prevent inadvertent movement of the terminal pin along the longitudinal axis out from within the connector housing opening.

2. The feedthrough connector assembly of claim 1, which comprises a feedthrough capacitor, comprising:
   a) a dielectric body;
   b) at least one active electrode plate and at least one ground electrode plate encased in the dielectric body in spaced relation with each other;
   c) at least one second bore extending through the dielectric body;
   d) at least one first electrically conductive material disposed in the second bore to conductively couple the terminal pin to the active electrode plate; and
   e) at least one second electrically conductive material contacting an outer surface of the dielectric body to electrically couple the ground electrode plate to the conductive ferrule;
   f) wherein the hermetic feedthrough is connected to the feedthrough capacitor and are electrically connected to the connector with the first terminal pin portion extending into the housing opening and proximate the housing end sidewall so that the prong end contacts the terminal pin sidewall in a grip-tight engagement to thereby help prevent inadvertent movement of the terminal pin along the longitudinal axis out from within connector opening.

3. The feedthrough connector assembly of claim 1 wherein the inner housing surface extends from the first diameter to an end wall within the connector housing, thereby forming a blind hole therewithin.

4. The feedthrough connector assembly of claim 1 wherein the feedthrough comprises a first braze material hermetically sealing the terminal pin to the insulator in the terminal pin bore and a second braze material hermetically sealing the insulator to the ferrule.

5. The feedthrough connector assembly of claim 1 wherein a recess extends partially within an exterior sidewall surface of the terminal pin so that the prong end contacts within the recess of the terminal pin sidewall in a grip-tight engagement to thereby help prevent inadvertent movement of the terminal pin along the longitudinal axis out from within connector opening.

6. The feedthrough connector assembly of claim 1 wherein a ridge extends outwardly from an exterior sidewall surface of the terminal pin so that the prong end contacts a portion of the exterior terminal pin surface distal of the ridge in a grip-tight engagement to thereby help prevent inadvertent proximal movement of the terminal pin along the longitudinal axis out from within connector opening.

7. The feedthrough connector assembly of claim 1 wherein at least an exterior surface of the connector housing comprises an electrically conductive material.

8. The feedthrough connector assembly of claim 1 wherein at least an exterior surface of the connector housing comprises a material selected from the group consisting of copper, tin, gold, platinum, palladium, titanium, and combinations thereof.

9. The feedthrough connector assembly of claim 1 wherein the terminal pin is composed of a material selected from the group consisting of platinum, platinum alloys, gold, silver, palladium, palladium alloys, niobium and tantalum.

10. The feedthrough connector assembly of claim 1 wherein the connector housing is configured for electrical connection to a circuit board.

11. The feedthrough connector assembly of claim 1 wherein the insulator is composed of a material selected from the group consisting of alumina, zirconia, zirconia toughened alumina, aluminum nitride, boron nitride, silicon carbide, glass and combinations thereof.

12. The feedthrough connector assembly of claim 1 wherein the electrically conductive ferrule is selected from the group consisting of titanium, tantalum, niobium, stainless steel, and combinations thereof.

13. The feedthrough connector assembly of claim 1 wherein the exterior surface of the connector housing is configured to be joined to a circuit board.

14. The feedthrough connector assembly of claim 1 wherein the connector further comprises an inner base portion, the inner base portion having a second diameter less than the first diameter and a second length that is less than the first length of the housing sidewall, and wherein the at least one prong is supported by the base portion in the connector housing opening.

15. The feedthrough connector assembly of claim 14 wherein a portion of the pin sidewall is wedged against a surface of the base portion to establish a grip-tight engagement to thereby help prevent inadvertent movement of the terminal pin within connector opening.

16. The feedthrough connector assembly of claim 14 wherein the base portion of the connector has an annular shape about the connector housing opening.

17. A method for positioning a feedthrough assembly within an implantable medical device, comprising the steps of:
   a) providing an electrically conductive connector, comprising:
      i) a connector housing comprising a housing sidewall defining an opening surrounded by an inner surface of the housing sidewall, wherein the inner housing surface has a first length extending along a longitudinal axis to opposed first and second housing ends and wherein the inner housing surface has a first diameter for at least part of the first length; and
      ii) at least one prong supported by the housing sidewall in the opening, wherein the prong extends axially and inwardly along the longitudinal axis to a prong end that is closer to the axis than the first diameter of the inner housing surface;
   b) providing a hermetic feedthrough, comprising:
      i) an electrically conductive ferrule comprising a ferrule sidewall having an inner ferrule surface defining a ferrule opening, wherein the ferrule sidewall extends from a first ferrule end surface spaced from a second ferrule end surface;
      ii) an insulator disposed at least partially within and hermetically sealed to the inner ferrule surface, wherein the insulator comprises first and second insulator ends disposed adjacent to the respective first and second ferrule end surfaces;
      iii) at least one first bore extending through the insulator to the first and second insulator ends;
      iv) an electrically conductive terminal pin received in the first bore, the terminal pin having a terminal pin sidewall extending from a first terminal pin portion having a first terminal pin end to a second terminal pin end, wherein the opposed first and second terminal pin ends are spaced outwardly from the respective first and second insulator ends; and v) a first braze material hermetically sealing the terminal pin to the insulator and a second braze material hermetically sealing the insulator to the ferrule; and c) moving the hermetic feedthrough in a first direction along the longitudinal axis to provide the first terminal pin portion extending into the opening of the connector with the prong end contacting the terminal pin sidewall in a grip-tight engagement, thereby preventing inadvertent movement of the terminal pin in a second, opposite direction along the axis out from within the connector opening.

18. The method of claim 17 including providing a feedthrough capacitor, comprising:
a) a dielectric body;
b) at least one active electrode plate and at least one ground electrode plate encased in the dielectric body in spaced relation with each other;
c) at least one second bore extending through the dielectric body;
d) at least one first electrically conductive material disposed in the second bore to conductively couple the terminal pin to the active electrode plate; and
e) at least one second electrically conductive material contacting an outer surface of the dielectric body to electrically couple the ground electrode plate to the conductive ferrule; and
f) electrically connecting the feedthrough capacitor to the hermetic feedthrough.

19. The method of claim 17 including providing a blind hole that extends within the connector housing from the first diameter to an end wall along the first length.

20. The method of claim 17 including providing an electronic circuit board supported in a first case half for an implantable medical device, wherein the connector is electrically connected to an electrical contact on the circuit board.

21. The method of claim 17 including joining the connector housing to the electrical contact using soldering or welding.

22. The method of claim 17 including providing a recess that extends at least partially within an exterior sidewall surface of the terminal pin so that the prong end contacts within the recess of the terminal pin sidewall in a grip-tight engagement to thereby help prevent inadvertent movement of the terminal pin along the longitudinal axis out from within connector opening.

23. The method of claim 17 including providing a ridge that outwardly extends from an exterior sidewall surface of the terminal pin so that the prong end contacts a portion of the exterior surface position distal of the ridge in a grip-tight engagement to thereby help prevent inadvertent proximal movement of the terminal pin along the longitudinal axis out from within connector opening.

24. The method of claim 17 including constructing the connector housing, the base portion and the at least one prong from a material selected from the group consisting of copper, tin, gold, platinum, palladium, titanium, and combinations thereof.

25. The method of claim 17 including providing a second case half positioned adjacent the first case half, the first and second case halves joined together to support the feedthrough in a hermetic relationship between an interior of the joined case halves and an ambient environment outside thereof such that the connector is sealed within the joined first and second case halves.

26. The method of claim 17 including providing the base portion of the connector having an annular shape about the throughbore.

27. A feedthrough connector assembly, which comprises:
a) an electrically conductive connector, comprising:
i) a connector housing comprising a housing sidewall defining an opening surrounded by an inner surface of the housing sidewall, wherein the inner housing surface has a first length extending along a longitudinal axis to opposed first and second housing ends, wherein the inner housing surface defines the opening that extends from a first diameter at the first housing end to a second location proximate a connector housing sidewall end located at the second end; and
ii) at least one prong supported by the housing sidewall in the opening, wherein the prong extends axially and inwardly along the longitudinal axis to a prong end that is closer to the axis than the first diameter of the inner housing surface;
b) a hermetic feedthrough, comprising:
i) an electrically conductive ferrule comprising a ferrule sidewall having an inner ferrule surface defining a ferrule opening, wherein the ferrule sidewall extends from a first ferrule end surface spaced from a second ferrule end surface;
ii) an insulator disposed at least partially within and hermetically sealed to the inner ferrule surface, wherein the insulator comprises first and second insulator ends disposed adjacent to the respective first and second ferrule end surfaces;
iii) at least one first bore extending through the insulator to the first and second insulator ends;
iv) an electrically conductive terminal pin received in the first bore, the terminal pin having a terminal pin sidewall extending from a first terminal pin portion having a first terminal pin end to a second terminal pin end, wherein the opposed first and second terminal pin ends are spaced outwardly from the respective first and second insulator ends; and
v) a first hermetic seal at the terminal pin to the insulator and a second hermetic seal at the insulator to the ferrule; and
c) wherein the terminal pin of the hermetic feedthrough is electrically connected to the connector with the first terminal pin portion extending into the opening so that the prong end contacts the terminal pin sidewall in a grip-tight engagement to thereby help prevent inadvertent movement of the terminal pin along the longitudinal axis out from the connector opening.

28. The feedthrough connector assembly of claim 27 wherein the connector further comprises an inner base portion of the housing sidewall, the inner base portion having a second diameter less than the first diameter and a second length that is less than the first length of the housing sidewall, and wherein the at least one prong is supported by the base portion in the opening.

29. The feedthrough connector assembly of claim 27 wherein the feedthrough comprises a first braze material hermetically sealing the terminal pin to the insulator in the terminal pin bore and a second braze material hermetically sealing the insulator to the ferrule.

30. The feedthrough connector assembly of claim 27 further comprising a feedthrough capacitor, the feedthrough capacitor comprising:
 a) a dielectric body;
 b) at least one active electrode plate and at least one ground electrode plate encased in the dielectric body in spaced relation with each other;
 c) at least one first electrically conductive material conductively coupling the terminal pin to the active electrode plate; and
 d) at least one second electrically conductive material electrically coupling the ground electrode plate to the conductive ferrule.

31. The feedthrough connector assembly of claim 27 wherein at least an exterior surface of the connector housing comprises a material selected from the group consisting of copper, tin, gold, platinum, palladium, titanium, and combinations thereof.

32. The feedthrough connector assembly of claim 27 wherein the terminal pin is composed of a material selected from the group consisting of platinum, platinum alloys, gold, silver, palladium, palladium alloys, niobium and tantalum.

33. The feedthrough connector assembly of claim 27 wherein the connector housing is configured for electrical connection to a circuit board.

34. The feedthrough connector assembly of claim 27 wherein the insulator is composed of a material selected from the group consisting of alumina, zirconia, zirconia toughened alumina, aluminum nitride, boron nitride, silicon carbide, glass and combinations thereof.

35. The feedthrough connector assembly of claim 27 wherein the electrically conductive ferrule is selected from the group consisting of titanium, tantalum, niobium, stainless steel, and combinations thereof.

36. The feedthrough connector assembly of claim 27 wherein a recess extends partially within an exterior sidewall surface of the terminal pin so that the prong end contacts within the recess of the terminal pin sidewall in a grip-tight engagement to thereby help prevent inadvertent movement of the terminal pin along the longitudinal axis out from within connector opening.

37. The feedthrough connector assembly of claim 27 wherein a ridge extends outwardly from an exterior sidewall surface of the terminal pin so that the prong end contacts a portion of the exterior surface position distal of the ridge in a grip-tight engagement to thereby help prevent inadvertent proximal movement of the terminal pin along the longitudinal axis out from within connector opening.

\* \* \* \* \*